United States Patent [19]
Collins

[11] Patent Number: 4,781,188
[45] Date of Patent: Nov. 1, 1988

[54] UMBILICAL CORD CLAMP APPARATUS

[76] Inventor: Jason H. Collins, 2986 Palm Dr., Slidell, La. 70458

[21] Appl. No.: 909,883

[22] Filed: Sep. 22, 1986

[51] Int. Cl.⁴ .............................................. A61B 17/10
[52] U.S. Cl. ..................................... 128/305; 128/346; 30/136
[58] Field of Search ............... 128/305, 318, 319, 325, 128/326, 334 C, 346, 361; 30/124, 136, 136.5; 24/633; 251/9, 10

[56] References Cited

U.S. PATENT DOCUMENTS

| | | | |
|---|---|---|---|
| 2,524,337 | 10/1950 | Whittaker | 128/346 |
| 4,026,294 | 5/1977 | Mattler | 128/346 |
| 4,212,303 | 7/1980 | Nolan | 128/346 |
| 4,425,689 | 1/1984 | Fildan | 24/633 |
| 4,428,374 | 1/1984 | Auburn | 128/346 |
| 4,572,181 | 2/1986 | Mattler | 128/346 |
| 4,602,629 | 7/1986 | Schnirman | 128/346 |
| 4,648,401 | 3/1987 | Mattson | 128/325 |

Primary Examiner—Dalton L. Truluck
Assistant Examiner—Frank Wilkens
Attorney, Agent, or Firm—Pravel, Gambrell, Hewitt, Kimball & Krieger

[57] ABSTRACT

An umbilical cord clipper apparatus constructed of non-metallic material having a base portion and a top portion movable between open and closed positions in relation to one another via a loop hinge on their common end portion. The apparatus further comprises first and second recesses in the base and top portion for positioning of an umbilical clamp of the type which would incorporate a pair of elongated arms and a loop portion as disclosed in U.S. Pat. No. 3,854,482. The pair of clamps are positioned with a space therebetween, so that a blade member housed in the floor of the base portion, flies intermediate the two clamp members positioned therein. Further, there is provided a pair of flexing members within the hinged loop so that the clamp when in position within the base of the apparatus are engaged against the bias of the members.

6 Claims, 1 Drawing Sheet

U.S. Patent
Nov. 1, 1988
4,781,188
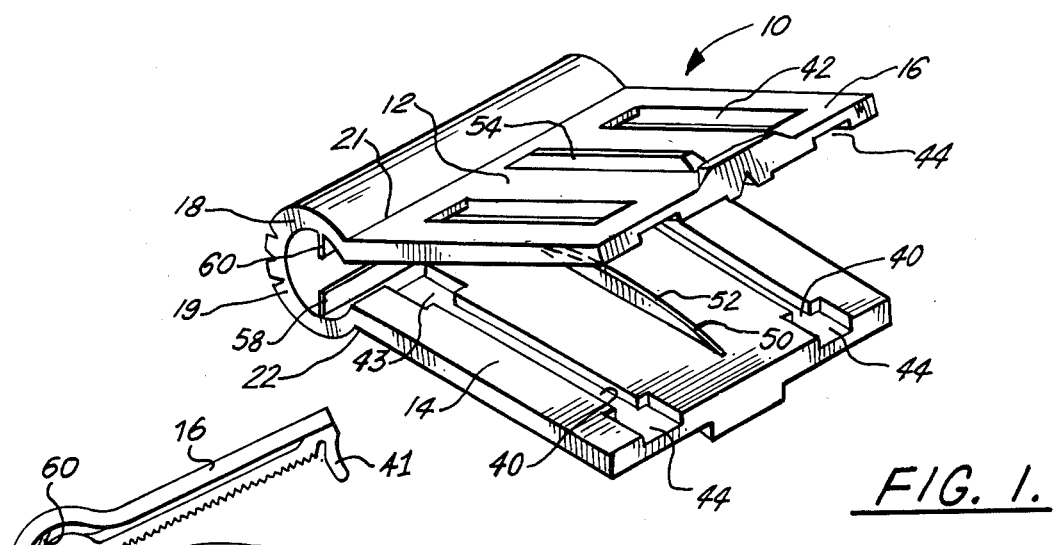
FIG. 1.
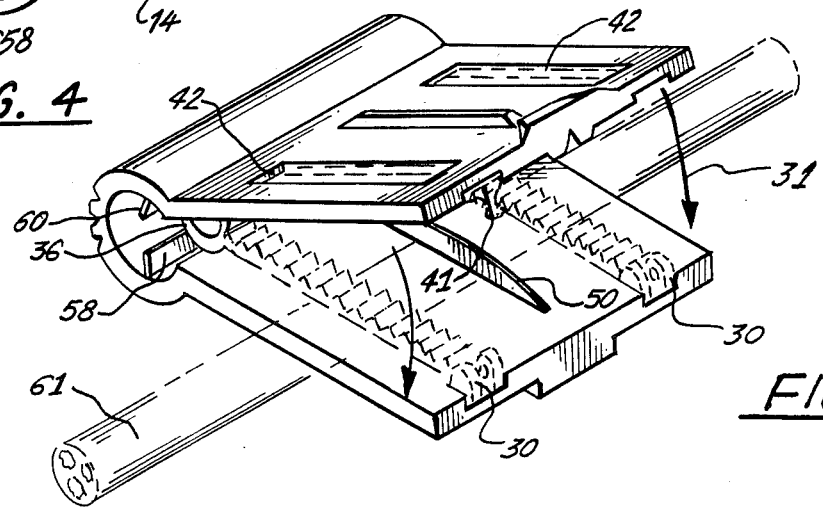
FIG. 4.
FIG. 2.
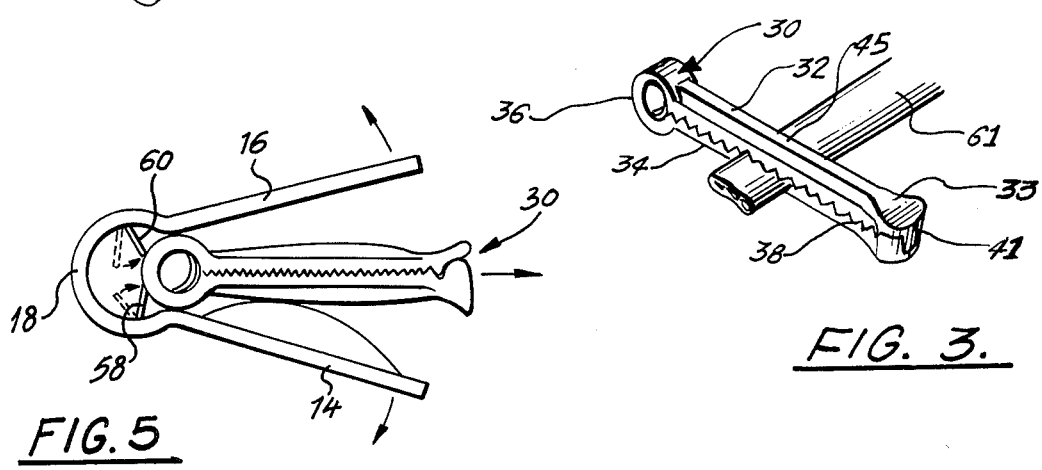
FIG. 5.
FIG. 3.

UMBILICAL CORD CLAMP APPARATUS

BACKGROUND OF THE INVENTION

1. Field of the Invention

The apparatus of the present invention relates to clamps. More particularly, the present invention relates to an apparatus for severing and clamping both severed ends of the umbilical cord of a newly born infant in a single step.

2. General Background

In the science of the delivery of babies, following the removal of the baby from the mother, it is necessary that the umbilical cord, through which the baby is receiving its blood supply and nutrients from the mother, is severed, and the loss of blood from the cord be interrupted. Therefore, in the present state of the art, this procedure is basically accomplished in three steps. First, the cord is clamped with two separate clamps, with a space between the clamps, and the third step is that the cord is then severed. Therefore, no blood is lost either from the baby nor from the mother's placenta, and the baby's cord is then permanently tied off, and the placenta is then removed from the mother to prevent any further loss of blood.

Practice has it that this obstetric procedure during the delivery of the baby is somewhat time consuming, and may be simplified. It would therefore be beneficial to the servicing physician, that following the delivery of the baby, that there be an instrument which would enable the physician to quickly clamp and cut the cord through perhaps a single step, which would eliminate any of the unnecessary steps which are now undertaken.

In addressing the question of this type, several patents have been issued, the most pertinent being as follows:

U.S. Pat. No. 3,315,679 issued to Sarracino, entitled "Umbilical Cord Clamp", simply teaches the use of a single clamp which provides jaw faces on which faces are formed complementary, serrated, ungulated surfaces. A spring or the like is provided for resiliently biasing the surfaces toward one another in engagement with the umbilical stump.

U.S. Pat. No. 3,040,749 issued to Paten, entitled "Umbilical Cord Clamp", likewise provides an expendable and disposable umbilical cord clamp apparatus which has generally parallel clamping members when the clamp is closed, and has a permanently lock that can not be released following the closing of the clamp.

U.S. Pat. No. 2,307,377 issued to Riccardi, entitled "Umbilical Clip", also teaches the use of a clip which can be placed upon a pair of forceps or the like, and upon engaging the clamping member in locking the clamp in place, the forceps are removed and the clamp remains on the umbilical cord.

U.S. Pat. No. 2,626,608 issued to Garland, entitled "Clamp For Umbilical Cords Or The Like", likewise teaches the use of a clamp which can be place upon a pair of pliers and once engaged, the plyer member bend into a position that remains in the clamped position during use.

U.S. Pat. No. 3,705,586 issued to Sarracino, entitled "Umbilical Cord Clamp", addresses the use of an umbilical clamp having serrated edges that because of the edges and the inner locking of the clamp will remain in place over a period of days.

U.S. Pat. No. 1,710,766 issued to Dilworth, entitled "Umbilical Cord", relates to an umbilical clamp which is slipped onto the umbilical cord and is clamp into place while simultaneously severing the umbilical cord at the joint of clamping.

U.S. Pat. No. 1,843,652 issued to Taylor, entitled "Umbilical Cord Clamp", in which two pieces of sheet metal or pivoted on one another being held flatly in place by means of a pivotal pin. Each of the pieces of metal having a cut out which constitutes jaws of the clamp and effects closure of the cut joint opening which exists when the cut outs overlay one another.

U.S. Pat. No. 2,948,372 issued to Kortlucke, Jr., et at, entitled "Clamping Device", also teaches the use of a clamp of the type that has serrated edges and closes upon the item to be clamped with it locking in place around the second end portion.

U.S. Pat. No. 2,434,831 issued to Brandenburg, entitled "Umbilical Clip And Holder For Same", teaches the use of an umbilical clip which is placed in position on a pair of forceps; after clamping takes places the forceps are removed therefrom with the clamp being maintained in the closed position.

U.S. Pat. No. 2,524,377 issued to Whittaker, entitled "Umbilical Clamp And Cutter", relates to a clamp for simultaneously clamping the umbilical cord at two spaced points in cutting the cord between the clamped points.

U.S. Pat. No. 3,854,482 issued to Laugherty, et al, entitled "Umbilical Cord Clamp", teaches the use of an umbilical cord clamp made of non-metallic material with a pair of elongated arms joined at a hinged loop and a locking means on the second hand for locking the clamp in the closed position following clamping around the cord.

SUMMARY OF THE PRESENT INVENTION

The apparatus of the present invention solves the shortcomings in the art in a simple and straightforward manner. What is provided is an umbilical cord clipper apparatus constructed of non-metallic material having a base portion and a top portion movable between open and closed positions in relation to one another via a loop hinge on their common end portion. The apparatus further comprises first and second recesses in the base and top portion for the positioning of an umbilical clamp of the type which would incorporate a pair of elongated arms and a loop portion as disclosed in U.S. Pat. No. 3,854,482. The pair of clamps are positioned with a space there between, so that a blade member housed in the floor of the base portion, lies intermediate the two clamp members positioned therein. Further, there is provided a pair of flexing members within the hinged loop so that the clamp when in position within the base of the apparatus are engaged against the bias of the members. In use, the umbilical cord is positioned within the space between the upper and lower portions of the apparatus, the apparatus is moved to the closed position wherein the centrally located blade severs the umbilical cord and simultaneously the clamp members are engaged in the closed position on either side of the cut, and upon opening the apparatus, the clamps remain in the closed position and are disengaged from the apparatus through the force of the flexing members within the hinge loop, and the apparatus housing is removed therefrom for disposal, with the clamps remaining in the closed position on the severed ends of the cord.

BRIEF DESCRIPTION OF THE DRAWINGS

FIG. 1 is an isometric view of the preferred embodiment of the apparatus of the present invention;

FIG. 2 is an isometric view of the apparatus of the present invention illustrating an umbilical cord positioned therein;

FIG. 3 illustrates the clamp portion of the apparatus clamped in place around a severed umbilical cord;

FIG. 4 is a side view of the preferred embodiment of the apparatus of the present invention containing a clamp in position within the holder apparatus; and FIG. 5 is a side view of the preferred embodiment of the apparatus of the present invention following the clamp portion of the apparatus being clamped in place around a severed umbilical cord, and the holder being reopened for removal of the holder.

DETAILED DESCRIPTION OF THE PREFERRED EMBODIMENT

FIGS. 1–3 illustrate the preferred embodiment of the apparatus of the present invention. The present invention wil be illustrated by the numeral 10. In FIG. 1, the housing portion is illustrated of the composite apparatus 10. Housing portion 12 comprises a unitary non-metallic material housing which includes a base portion 14 and an upper portion 16, the upper portion 16 and base portion 14 substantially identical in rectangular shape, and movable between a first open position as seen in FIG. 1, and a second closed position movable in the direction of Arrows 31 as seen in FIG. 2. The movement of the base portion 14 and the top portion 16 in relation to one another between open and closed positions is affected by a loop hinge portion 18 which comprises a substantially circular loop member 19 integrally joined to define the back edge 21 of top portion 16 and the back edge 22 of the base portion 14, so that the top portion 16 would be normally in the open position as seen in FIG. 1, and would have to be forceably moved to the closed position against the bias of hinge loop 18 when in use.

Reference is now made to FIG. 2, which illustrates in composite illustration, the apparatus housing a pair of clamp members 30 of the type as illustrated in FIG. 3. The clamp members 30 being of the type having a pair of arms 32 and 34 which extend lengthwise of each other and may be made of a suitable plastic material, of the type disclosed in U.S. Pat. No. 3,854,482. Likewise, the cord clamp 30 as initially formed, is in the open position substantially as seen in FIG. 2, and any closing of the clamp would be against the bias of a hinge loop 36 on clamp member 30. Preferably, the clamp members would contain a plurality of teeth 38 which would facilitate gripping of the umbilical cord and would engage adjacent one another as seen in FIG. 3 during the clamping process. Likewise, clamp 30 would have a locking member 41 on its end portion so that when the clamp is locked in position, the locking member is unable to be opened and would remain clamped as seen in FIG. 3. Further, for purposes of construction, clamp member 30 would also include an extended dorsal ridge 42 along its upper clamp portion 31, the function of which for use in the housing 12 would be of some importance.

Returning now to FIG. 1, it is noted that both the base portion of apparatus 10 includes a pair of channels 40 and 42 which are so constructed so as to have a rear boxed recessed portion 43 and a front boxed portion 44, with the extended channel 42 therebetween. Likewise, the top portion would likewise have a front box recessed portion 44 and a rear boxed recessed portion 43 (which are not seen in the FIGS.), and likewise would have an inner connecting channel 42 therebetween. However, for purposes of this construction, the upper channel 42 forms a continuous length wise window 42 in the top portion of the apparatus, the function of which will be discussed further.

Further in terms of construction, since the apparatus is utilized for both clamping the cord and severing the cord simultaneously, there is provided a vertically positioned blade member 50 which, for purposes of illustration in FIG. 1, has an acute cutting edge 52 for more complete severing of the cord, and so that the housing can be fully closed during use, there is further positioned an internal channel 54 on the upper portion 16 having a groove therein for housing blade 50 when the clamp is in the closed position.

Turning now to FIG. 2, it should be noted in FIG. 2, FIG. 2 illustrates the combination of housing 12 which is housing a pair of clamps 30, of the type illustrated in FIG. 3. It should be noted that front box portion 44 houses the front portion of clamp 30, with the body portion of clamp 30 resting within channels 42, and the rear hinge loop 36 resting partially in rear box recessed 43.

However, since it is necessary that upon opening of housing 12 after clamp members 30 have been locked in place as seen in FIG. 3, and for the easy removal of housing 12 following this step, there must be provided a means for assisting in releasing the clamp 30 from the housing 12 after the housing is reopened to the position in FIG. 1. Reference is made to FIGS. 4 and 5 which clearly illustrates a means for assisting in the removal of the clamp member after the clamp has been clamped into position around the severed umiblical cord, so that when the housing 12 is moved to the open position as seen in FIG. 5, the clamp members 30 are removed from the housing 12 through this means. This means includes a pair of flexible members 58 and 60 as seen in FIGS. 1, 2, 4 and 5, which are housed within curved hinge 18 and upon positioning of the clamp members 30 as seen in FIG. 2, the rear portion of the curved hinge 36 of clamp members 30 exert force against the members 58 and 60 and are actually held in position against bias of these two members. Assisting to hold the clamps within the housing so that they are not forced out under the force of members 58 and 60, the upper ridge member 42 of clamp 30 as was discussed earlier, is set into the upper lengthwise housing window 42 of upper portion 16 as seen in FIG. 2, thus maintaining the clamp "locked" in place while the clamp housing is in the open position. As seen in FIG. 2, upon placement of an umbilical cord 61 transversely across blade 50, as seen in FIG. 2, upper portion 16 of housing 12 is moved in the down position as seen by Arrows 31, and upon being closed fully, blade 50 severs umbilical cord 61, and simultaneously clamp lock members 30 lock in place around umbilical cord 61. Upon movement of clamp housing upper portion 16 to the up position as in FIG. 1, ridge 43 has disengaged from channel 42, and therefore members 58 and 60 resiliently help to disengage clamp members 30 from housing 12 so that housing 12 maybe disposed of. The end result, of course, as seen in FIG. 3 with both severed ends of umbilical cord 60 clamped off in order to prevent bleeding.

Therefore, this apparatus enables one to achieve the clamping and cutting of the umbilical cord in a simple step, and with the particular construction of the housing 12, the apparatus is able to be easily disengaged from the clamps once the clamp is in position, and it maybe this easily discarded. For purposes of manufacturing, the clamp housing as with the clamps may be molded of a unitary type plastic material with a surgical type blade therewith for inexpensive manufacture yet very useful in nature.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A composite umbilical cord cutter and clamp apparatus, comprising:
   a. a base member having an upper and lower portion, the upper and lower portion joined by a loop integral therewith so that the opposite ends are normally spaced apart and may move between open and closed positions in relation to one another;
   b. means contained on the base member for engaging and supporting at least a pair of clamp members in spaced relation, each of said clamp members further comprising a substantially V-shaped portion including a pair of arms joined together by a loop integral therewith forming a hinge between the arms at one end with the opposite ends being freely and normally spaced apart, the arms movable between a first unclamping open position and a second clamped position, and locking means on each of the members for maintaining each of the members in the locked position;
   c. cutting means on the base member positioned intermediate the clamp members for severing the umbilical cord following the movement of the base member and clamp members to the second clamped position; and
   d. upper and lower resilient retainer plates positioned in the loop of the base member for assisting in releasing the clamp members from the base member following the return of the base member to the open position.

2. The apparatus in claim 1, wherein the means contained in the housing member for housing a pair of clamp members further comprises a pair of recesses contained within the housing for maintaining the clamp members in the secure position during clamping.

3. The apparatus in claim 1, wherein there is further provided means in the upper portion of the base member for receiving the cutting means when the base member is in the closed position.

4. The apparatus in claim 1, wherein the cutting means further comprises an acute blade extruding from the lower portion of the apparatus, to a degree to completely sever an umiblical cord placed thereupon when the clamp is placed in the closed position.

5. A composite umbilical cord cutter and clamp apparatus, comprising:
   a. a base member having an upper portion and a lower portion, the upper and lower portions joined by at one end integral to the upper and lower portions, by a flexible hinge for moving the upper and lower portions between open and closed positions;
   b. means contained on the upper and lower portions of the base member, for engaging and supporting a pair of clamp members in spaced relation, the clamp members being of the type to clamp across and prevent fluid flow through the umbilical cord when the clamp members are placed in a clamped position by moving the base member to the closed position;
   c. a cutting blade secured into the lower portion of the base member, extruding a distance sufficient to sever an umbilical cord when the clamp members are moved to the clamped position by the closing of the base member; and
   d. upper and lower resilient retainer plates positioned adjacent the hinge of the base member for assisting in releasing the pair of clamp members from within the base member following return of the base member to the open position while the clamp members are in the clamped positioned following severing of the umbilical cord.

6. A composite umbilical cord cutter and clamp apparatus, for housing a pair of umbilical clamps, each of the type being a V-shaped member having a pair of arms joined together by a resilient loop integral therewith for defining a hinge between the arms at a first end, the second end being freely and normally spaced apart, and a locking member on the second end for maintaining each clamp in the locked position, the apparatus comprising:
   a. a base member having an upper portion and a floor portion, the upper portion and floor portion joined at an apex by a flexible loop so that the opposite ends of the upper portion and the floor portion are normally spaced apart and are able to move between open and closed positions;
   b. means contained on the base member, for securing the clamp members on the base member in spaced apart relationship;
   c. cutting means positioned in the floor portion of the base member and intermediate the clamp members, and extruding upward from the floor portion a distance sufficient to completely sever an umbilical cord, when the upper portion and the floor portion of the base member are moved to the closed position; and
   d. upper and lower resilient retainer plates formed in the flexible loop of the base member for assisting to force the clamp members from the base member following the return of the upper portion and floor portion from the closed position to the open position.

* * * * *